United States Patent
Chambers, Jr. et al.

(10) Patent No.: US 6,709,613 B2
(45) Date of Patent: Mar. 23, 2004

(54) PARTICULATE ADDITION METHOD AND APPARATUS

(75) Inventors: Leon Eugene Chambers, Jr., Marietta, GA (US); Eric Edward Lennon, Roswell, GA (US); Gabriel Hamman Adam, Alpharetta, GA (US); Jerome Joseph Schwalen, Marietta, GA (US); Christopher Andrew Laslie, Cumming, GA (US); H. Edmund Clark, Owensboro, KY (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 218 days.

(21) Appl. No.: 10/036,854

(22) Filed: Dec. 21, 2001

(65) Prior Publication Data

US 2003/0116890 A1 Jun. 26, 2003

(51) Int. Cl.⁷ .................................................. A61F 13/15
(52) U.S. Cl. ................... 264/121; 264/518; 264/122; 425/80.1; 425/83.1
(58) Field of Search ................. 264/518, 121, 264/122; 425/80.1, 83.1

(56) References Cited

U.S. PATENT DOCUMENTS

| | | | |
|---|---|---|---|
| 3,802,817 A | 4/1974 | Matsuki et al. |
| 3,901,236 A | 8/1975 | Assarsson et al. |
| 4,076,663 A | 2/1978 | Masuda et al. |
| 4,100,324 A | 7/1978 | Anderson et al. |
| 4,278,113 A | 7/1981 | Persson |
| 4,286,082 A | 8/1981 | Tsubakimoto et al. |
| 4,340,563 A | 7/1982 | Appel et al. |
| 4,352,649 A | 10/1982 | Jacobsen et al. |
| 4,375,448 A | 3/1983 | Appel et al. |
| RE31,775 E | 12/1984 | Persson |
| 4,494,278 A | 1/1985 | Kroyer et al. |
| 4,530,353 A | 7/1985 | Lauritzen |
| 4,640,810 A | 2/1987 | Laursen et al. |
| 4,756,969 A | 7/1988 | Takeda |
| 4,813,948 A | 3/1989 | Insley |

(List continued on next page.)

FOREIGN PATENT DOCUMENTS

| | | | |
|---|---|---|---|
| EP | 0 509 708 A1 | 10/1992 | ............. C08F/8/14 |
| EP | 0 540 041 B1 | 5/1993 | |
| EP | 1 029 886 A2 | 8/2000 | |
| EP | 1 145 724 | 10/2001 | |
| GB | 2 196 343 A | 4/1988 | |

(List continued on next page.)

OTHER PUBLICATIONS

Translation of Japanese laid open application No. S63–73956, Apr. 1988.
Cavlin et al.: *A New Method for Measuring the Edgewise Compression Properties of Paper*, Svensk Papperstidning, No. 9, pp. 330–332, 1975.
Derwent Abstract; XP 002240776 & JP 58 019360 A; Feb. 4, 1983.

(List continued on next page.)

*Primary Examiner*—Mary Lynn Theisen
(74) *Attorney, Agent, or Firm*—Pauley Petersen & Erickson (57) ABSTRACT

A nonwoven web contains an even distribution of its composite materials by the separate application of particulate material such as superabsorbent particles into a forming head outside the air stream for deposition of thermoplastic fibers in the forming head. The thermoplastic fibers are distributed by air entertainment through tubular forming screens having rotary distribution members therein. The particulate absorbents are generally placed in the forming box by distribution units which may have metering devices and outlet chutes extending into the forming head.

32 Claims, 4 Drawing Sheets

U.S. PATENT DOCUMENTS

| | | | |
|---|---|---|---|
| 4,921,645 A | 5/1990 | Insley | |
| 5,002,814 A | 3/1991 | Knack et al. | |
| 5,145,351 A | 9/1992 | Rossi | |
| 5,230,959 A | 7/1993 | Young, Sr. et al. | |
| 5,246,770 A | 9/1993 | Bottiglione et al. | |
| 5,277,976 A | 1/1994 | Hogle et al. | |
| 5,368,918 A | 11/1994 | Harada et al. | |
| 5,418,045 A | 5/1995 | Pike et al. | |
| 5,445,777 A | 8/1995 | Noel et al. | |
| 5,466,409 A | 11/1995 | Partridge et al. | |
| 5,489,469 A | 2/1996 | Kobayashi et al. | |
| 5,527,171 A | 6/1996 | Soerensen | |
| 5,558,832 A | 9/1996 | Noel et al. | |
| 5,800,418 A | 9/1998 | Ahr | |
| 5,858,535 A | 1/1999 | Wang et al. | |
| 5,885,516 A | 3/1999 | Christensen | |
| 5,972,808 A | 10/1999 | Groeger et al. | |
| 5,981,410 A | 11/1999 | Hansen et al. | 442/361 |
| H1909 H | 11/2000 | Ahr | |
| 6,214,274 B1 | 4/2001 | Melius et al. | |
| 6,239,230 B1 | 5/2001 | Eckert et al. | 525/329.9 |
| 2001/0042948 A1 | 11/2001 | Sorensen | |

FOREIGN PATENT DOCUMENTS

| | | | | |
|---|---|---|---|---|
| WO | 81/02031 | 7/1981 | | |
| WO | 86/00097 | 1/1986 | | |
| WO | 87/01403 | 3/1987 | | |
| WO | WO 91/18042 | 11/1991 | | C08J/3/12 |
| WO | 95/18886 | 7/1995 | | |
| WO | WO 96/14885 | 5/1996 | | |
| WO | WO 97/27884 | 8/1997 | | |
| WO | 97/30223 | 8/1997 | | |
| WO | WO 98/48857 | 11/1998 | | |
| WO | WO 99/63923 | 12/1999 | | |
| WO | 00/59439 | 10/2000 | | |
| WO | WO 00/62825 | 10/2000 | | A61L/15/00 |
| WO | 00/62922 | 10/2000 | | |
| WO | WO 00/69383 | 11/2000 | | |
| WO | 00/78369 | 12/2000 | | |
| WO | WO 02/076520 A2 | 10/2002 | | |
| WO | WO 02/077347 A2 | 10/2002 | | |

OTHER PUBLICATIONS

Derwent Abstract; XP 002240768 & JP 61 055249 A; Mar. 19, 1986.

Derwent Abstract; XP 002240906 & KR 8 901 835 B; May 25, 1989.

Patent Abstracts of Japan; Jan. 21, 1994 & JP 05 263318 A; Oct. 12, 1993.

Bronkhorst et al.: *Deformation and Failure Behavior of Paper, Handbook of Physical Testing of Paper*, pp. 313–349, vol. 1, 2002.

Fellers et al.: *Edgewise Compression Strength of Paper, Handbook of Physical Testing of Paper*, pp. 481–503, vol. 1, 2002.

PARTICULATE ADDITION METHOD AND APPARATUS

BACKGROUND OF THE INVENTION

Personal care products typically are made with a top sheet material (also referred to as a cover sheet or liner), an absorbent core and a liquid impervious back sheet. Some may also have a surge layer or other specialized layers between the top sheet and absorbent core. Absorption of fluid, comfort and avoidance of leakage are the functions desired.

In the making of absorbent webs it is often desirable that a uniform distribution be accomplished across the web when placing the absorbents within the web structure. Such absorbents may include natural absorbents, including cellulosic material such as wood pulp, and superabsorbent materials, as are known in the art. If a uniform distribution is not achieved across the web, product absorbency may suffer, or material may be wasted in the making of the absorbent web.

In nonwoven airlaid materials, as known in the art, nonwoven web constituents are entrained into an air stream and deposited on a forming wire, or web, and subsequently fixed in place by various means, such as heating. However, uniform entrainment of the various constituent materials is often problematic. The thermoplastic fibers, thermoplastic binders, cellulosic or other absorbent fibers, and superabsorbent materials, may come in a variety of forms, such as substantially continuous fibers, staple fibers, liquids, and particulates. The constituent materials may further be in a variety of weights, sizes and morphologies, as will be known to those of skill in the art.

Various methods have been proposed to alleviate uneven deposition of constituent materials for the nonwoven web onto the forming wire. One such method, often called a Dan-Web process, is exemplified in U.S. Pat. No. 4,640,810, to Laursen et al., in which the constituent materials are air-entrained through two perforate screen chambers, or tubular forming screens, located inside a forming head. The forming screens have particle-distributing rotary members therein for dispersing the constituent materials through the screens into the forming head and onto the forming wire. U.S. Pat. No. 5,885,516, to Christensen et al., teaches a similar system of particle distribution but with superabsorbent powder being distributed by a separate chute located between the forming screens and substantially at the bottom thereof. It has been found that achieving the proper mix of air currents to obtain uniform distribution of the materials in such systems can be problematic. Particulate constituent materials such as the superabsorbents, may especially be caused to aggregate, leading to wasted materials, or unsatisfactory performance for use in personal care absorbent articles. Other problems may include long process equilibrium times resulting from particulate build-up in the forming pipes and excessive equipment wear due to the abrasive nature of certain particulates.

Bicomponent nonwoven filaments are known in the art generally as thermoplastic filaments which employ at least two different polymers combined together in a heterogeneous fashion. Instead of being homogeneously blended, two polymers may, for instance, be combined in a side-by-side configuration, so that a first side of a filament is composed of a first polymer "A" and a second side of the filament is composed of a second polymer "B." Alternatively, the polymers may be combined in a sheath-core configuration, so that an outer sheath layer of a filament is composed of a first polymer "A," and the inner core is composed of a second polymer "B." Other heterogeneous configurations are also possible.

Pulp fibers have been employed in certain absorbent applications to enhance the absorbency. U.S. Pat. No. 4,530,353, issued to Lauritzen, discloses pulp fibers in combination with staple length bicomponent fibers used in the manufacture of absorbent bandages. In that case, the fibers also contain high and low melting polymers. The staple length fibers are bonded together by melting only the lower melting component. Likewise, superabsorbent materials, alone or in combination with pulp such as taught in published application WO 00/62922 (U.S. Ser. No. 09/546,634), fibers have been employed in certain absorbent applications to enhance the absorbency.

There is a need or desire for an absorbent nonwoven web composite which exhibits good softness and strength with a high degree of absorbency. There is a further need to achieve a high degree of absorbent particle loading in a nonwoven web to economically and efficiently make highly absorbent webs for personal care absorbent articles. This need exists for diapers, training pants, wipes, and other personal care absorbent articles where comfort, strength, and absorbent performance are all important.

There remains a need in the art for improved distribution of constituent materials in the making of absorbent nonwoven webs and alternative means and methods for achieving such distribution. It is further desirable that such means and methods achieve a high degree of absorbent material concentration within the web when required for particular product applications.

SUMMARY OF THE INVENTION

In response to the discussed difficulties and problems encountered in the prior art, new methods and apparatuses has been discovered which may provide both a high degree of absorbent materials by weight within the web and uniform distribution of materials within the web. Personal care products using the resultant webs are also contemplated to be within the scope of this invention.

One such personal care product has a liquid impermeable backsheet, a liquid permeable topsheet, and an absorbent composite web located between the topsheet and backsheet. The absorbent composite web, hereinafter sometimes referred to simply as the web, according to one embodiment of the present invention, is a coformed web having major surfaces in the X-Y plane and a depth in the Z direction that is suitable for use as a fluid retention layer in a disposable absorbent article.

The web may contain a layer or layers of airlaid composite material which may have both thermoplastic fibers and absorbent material. The thermoplastic fibers desirably serve as a binder to the absorbent material. The thermoplastic fibers may be single component or multi-component fibers of various composition and may be present in amount of greater than or equal to about two weight percent in a web of binder fibers and absorbent materials.

The absorbent materials may be natural materials such as natural fibers including cellulosic materials such as staple fibers of wood pulp, or superabsorbent materials, or a combination of the natural and superabsorbent materials, and may be present in amounts of less than or equal to about ninety eight weight percent in a web of binder fibers and absorbent materials. The web may be provided with other layers such as forming tissues, films, or the like as desired for the ultimate product application of the web.

A method of achieving a web according to the present invention may include: passing the thermoplastic fibers and cellulosic fibers entrained in an airstream through tubular forming screens contained inside a forming head, the tubular forming screens having rotating distribution members within the tubular forming screens; and adding particulate superabsorbent within the forming head outside of, and/or above, the tubular forming screens with an air velocity substantially neutral to that of the forming head in order to avoid substantially interrupting the air flow within the forming head which might lead to uneven distribution of the web components. In another aspect of the present invention the method may include passing the thermoplastic fibers entrained in an airstream through tubular forming screens contained inside a forming head, and adding combined particulate superabsorbent and cellulosic fibers, or pulp-coated superabsorbents, within the forming head outside of, and above, the tubular forming screens with an air velocity substantially neutral to that of the forming head in order to avoid substantially disrupting the air flow within the forming head.

Apparatus for achieving the web according to the present invention may include means for entraining thermoplastic fibers and cellulosic fibers in an airstream; a forming head containing rotating tubular forming screens therein, the rotating tubular forming screens having means for accepting the airstream of entrained thermoplastic fibers and cellulosic fibers, the rotating tubular forming screens having rotating distribution members therein; and means for adding particulate superabsorbent within the forming head outside of the rotating tubular forming screens at locations upstream and downstream in the MD of the rotating tubular forming screens to avoid interrupting the air flow within the forming head which might lead to uneven distribution of the web components. In another aspect of the present invention the apparatus may include means for passing the thermoplastic fibers entrained in an airstream through tubular forming screens contained inside a forming head, and means for adding combined particulate superabsorbent and cellulosic fibers within the forming head outside of, and/or above, the tubular forming screens to avoid disrupting the air flow within the forming head. Such location may include placement of a chute outlet tangential to an upper quadrant of the tubular forming screens as further detailed below.

DEFINITIONS

"Particulate" as used herein includes all discrete particles including, but not limited to superabsorbents, and coated superabsorbents; and whether man-made or natural, and whether absorbent or nonabsorbent, and staple fibers, and excludes substantially continuous fibers.

"Disposable" includes being disposed of after a single use, or limited use, and not intended to be washed and reused.

A "layer" is defined as having a homogeneous composition and density, within typical process variability for nonwoven structures. Alternatively a layer may contain patterns within itself, such as stripes, apertures or waves. "Layer" when used in the singular may have the dual meaning of singular or plural elements. "Composite" is defined as having two or more components and may consist of one or more layers. These may be either homogeneous or heterogeneous.

As used herein and in the claims, the term "comprising" is inclusive or open-ended and does not exclude additional unrecited elements, compositional components, or method steps.

As used herein the term "nonwoven fabric or web" means a web having a structure of individual fibers or threads which are interlaid, but not in a regular and repeatable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

"Spunbond fibers" refers to small diameter fibers that are formed by extruding molten thermoplastic material as filaments from a plurality of fine capillaries of a spinneret. Such a process is disclosed in, for example, U.S. Pat No. 3,802,817 to Matsuki et al., U.S. Pat. No. 4,340,563 to Appel et al. The fibers may also have shapes such as those described, for example, in U.S. Pat. No. 5,277,976 to Hogle et al. which describes fibers with unconventional shapes.

The term "substantially continuous filaments" or "substantially continuous fibers" refers to filaments or fibers prepared by extrusion from a spinneret, including without limitation spunbond and meltblown fibers, which are not cut from their original length prior to being formed into a nonwoven web or fabric. Substantially continuous filaments or fibers may have average lengths ranging from greater than about 15 cm to more than one meter, and up to, or greater than, the length of the nonwoven web or fabric being formed. The definition of "substantially continuous filaments" (or fibers) includes those filaments or fibers which are not cut prior to being formed into a nonwoven web or fabric, but which are later cut when the nonwoven web or fabric is cut.

The term "staple fibers" means fibers which are natural or cut from a manufactured filament prior to forming into a web, and which have an average length ranging from about 0.1–15 cm, more commonly about 0.2–7 cm.

The term "superabsorbent material" refers to a water swellable, water-insoluble organic or inorganic material capable, under the most favorable conditions, of absorbing at least about 20 times its weight, preferably at least about 30 times its weight in an aqueous solution containing 0.9% by weight sodium chloride.

"Airlaying" is a well-known process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers then are bonded to one another using, for example, water spraying, calendering, hot air, or a spray adhesive. Airlaying is taught in, for example, U.S. Pat. No. 4,640,810 to Laursen et al. Airlaying may include coform deposition which is a known variant wherein pulp or other absorbent fibers are deposited in the superabsorbent material air stream onto the forming screen such as in U.S. Pat. No. 4,100,324 to Anderson et al. The screen may also be referred to herein as a forming wire.

"Personal care product" means diapers, wipes, training pants, absorbent underpants, adult incontinence products, feminine hygiene products, wound care items like bandages, and other articles.

Words of degree, such as "about", "substantially", and the like are used herein in the sense of "at, or nearly at, when given the manufacturing and material tolerances inherent in the stated circumstances" and are used to prevent the unscrupulous infringer from unfairly taking advantage of the invention disclosure where exact or absolute figures are stated as an aid to understanding the invention.

As used herein, the term "machine direction" or MD means the length of a fabric in the direction in which it is produced. The term "cross direction" or "cross machine direction" or CD means the width of fabric, i.e. a direction generally perpendicular to the MD in the same plane.

DETAILED DESCRIPTION

The absorbent webs of this invention may be made using the airlaid process. The production of airlaid nonwoven composites is well defined in the literature and documented in the art. Examples include the Dan-Web process as described in U.S. Pat. No. 4,640,810, to Laursen et al., assigned to Scan Web of North America Inc., and U.S. Pat. No. 5,885,516, to Christensen et al., assigned to Scan Web I/S of Denmark; the Kroyer process as described in U.S. Pat. No. 4,494,278, to Kroyer et al., and U.S. Pat. No. 5,527,171, to Soerensen, assigned to Niro Separation a/s, the method of U.S. Pat. No. 4,375,448, to Appel et al., assigned to Kimberly-Clark Corporation, or other similar methods.

Figure 1:
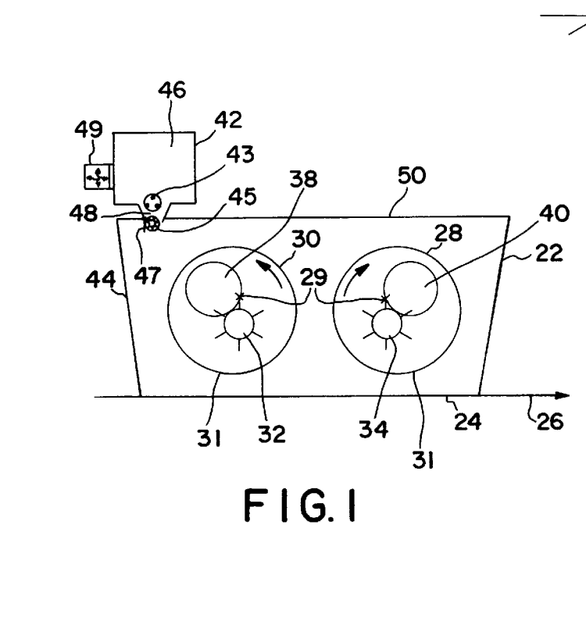
FIG. 1 is a schematic diagram of a first aspect of the present invention showing a Dan-Web type forming head with distribution means for absorbent particulates outside of, above, and upstream of the tubular forming screens.

As seen in FIG. 1, a cross sectional view of a Dan-Web type head modified according to one aspect of the present invention, a forming head 22 is placed above a foraminous forming wire 24. The wire 24 collects the deposited web components discharged by the forming head 22 and moves in the machine direction 26 as indicated by arrows. A Dan-Web type forming head will overlay the wire 24 and extend across the width, or cross machine direction 36 of the wire. The forming head 22 contains two counter-rotating tubular forming screens 28, 30 as indicated by the arrows thereon, having rotating distribution members 32, 34, one within each of the tubular forming screens 28, 30. The forming screens 28, 30 have a lower, or bottom-most surface, or point, 31 and rotate about their center points, collectively 29. The web component thermoplastic fibers and cellulosic fibers are entrained in an airstream and fed through opposing openings 38, 40 in the ends of the rotating tubular forming screens 28, 30 (contained inside the forming head 22) to the interiors of the rotating tubular forming screens 28, 30, to be distributed by the rotating distribution members 32, 34 back out through the forming screens and onto the wire 24.

Figure 5:
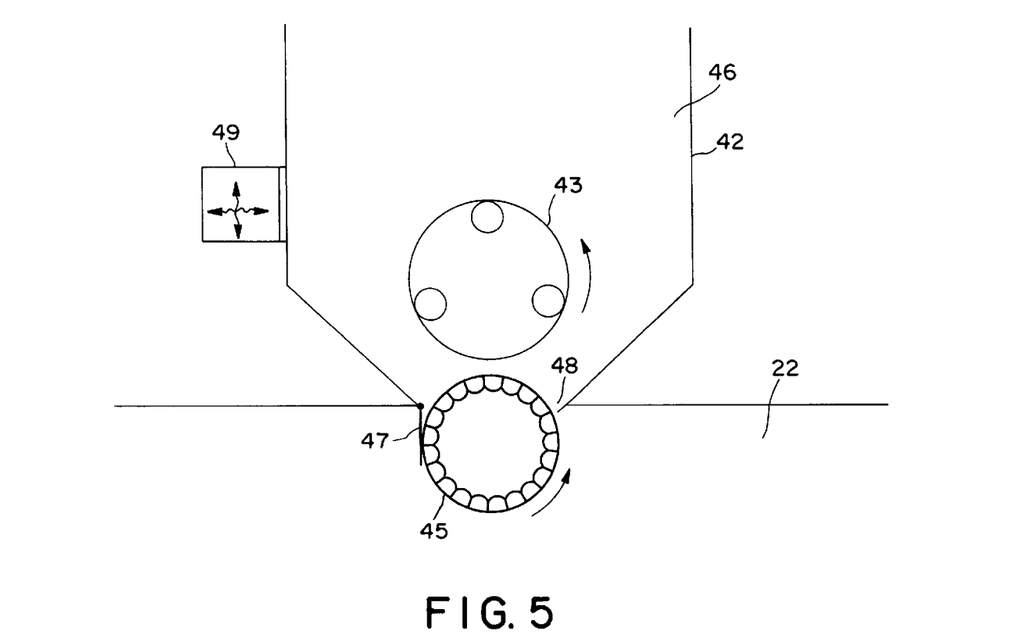
FIG. 5 is an enlarged view of the hopper and metering apparatus shown in FIG. 1.

The adding of particulates, e.g. such as superabsorbent particles, within the forming head 22 is done via a separate distribution unit 42 outside of the tubular forming screens 28, 30 at a location upstream in the MD, of the tubular forming screens, desirably at or near the upstream edge 44 of the forming head 22 and also desirably above the bottom-most surfaces 31 of the tubular forming screens 28, 30, and more desirably above the center points 29 of the tubular forming screens 28, 30. The distribution unit 42 may for example have a hopper 46 and outlet 48 which extend across the CD of the forming head 22 to deposit superabsorbents via a roller 45 through the top 50 of the forming head. Suitable distribution units may include particle feeders from Christy Machine Co. of Fremont, Ohio, under product designations "Christy Coat-O-Matic", Models: 20"-DI-S and 24"-DE-S(SP), and modified as shown in FIGS. 1 and 5. In order to produce an evenly metered and distributed flow of the particulate pulp-coated superabsorbent materials from the distribution unit 42 it may be desirable to place an agitator 43 within the hopper 46 in order to keep the superabsorbent materials in a free or non-agglutinated distribution when they are received by a metering/distribution means, such as the knurled roller 45 for eventual distribution through the outlet 48 into the cavity of the forming head 22. Further metering means may be added such as a wiper blade 47 contacting the knurled roller 45 as it carries the superabsorbent materials. The contact surfaces of wiper blade 47 may be constructed of silicone and may be in the form of a comb-type arrangement to gently wipe the excess superabsorbent materials from the knurled roller 47 while maintaining the integrity and distribution of the superabsorbent materials. A vibrator 49 may further be applied to the hopper 42 to aid in the flow of the particulate superabsorbent materials within the hopper 42.

Figure 2:
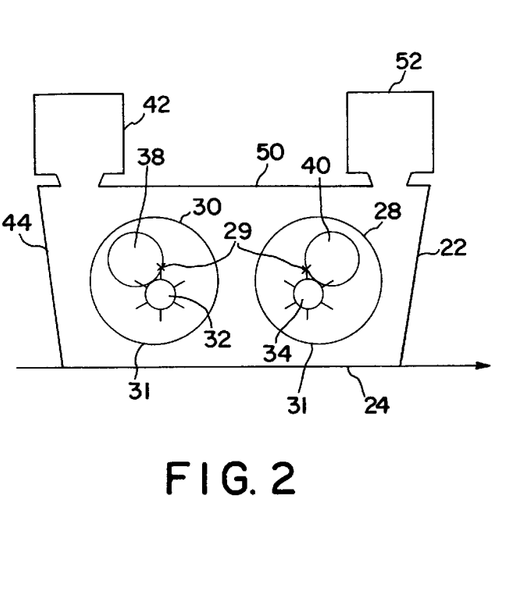
FIG. 2 is a schematic diagram of a second aspect of the present invention showing a Dan-Web type forming head with distribution means for absorbent particulates outside of, above, upstream and downstream of the tubular forming screens.

Referencing FIG. 2, an aspect of the present invention is shown wherein the particulates are added via both an upstream distribution unit 42 and a downstream distribution unit 52. The upstream distribution unit 42 and the downstream distribution unit 52 may operate to meter the flow of the particulates and may be operated concurrently, sequentially, or otherwise, such as to vary the amount, type, or placement of the particulates within the web.

By not sifting the particulates through the forming screens 28, 30, less particulate matter will be lost, particulate matter distribution will be made more even across the web, and equipment wear will be less. Higher line speeds/forming head throughput may also be achieved because all materials do not have to pass through the finite capacity tubular forming screens in order to produce a web. Further process enhancements will include quicker operation equilibrium times.

In one instance, an absorbent composite made according to the apparatus of FIG. 1 was a 323 gsm nonwoven web of 50 weight percent Stockhausen Favor 880 particulate superabsorbent from Stockhausen of Greensboro, N.C., 45 weight percent Buckeye Foley Fluff pulp from Buckeye Technologies, Inc. of Memphis, Tenn., and 5 weight percent KoSa Type 255 bicomponent binder fiber from KoSa Inc. (Charlotte, N.C.) (2.8 dpf and 0.25 inch length). In another instance absorbent composites made according to the apparatus of FIG. 1 were nonwoven webs varying between 142 to 400 gsm basis weight. KoSa Type 255 thermoplastic binder fiber was entrained to the forming screens 28, 30 while pulp-coated superabsorbent material particulates of 66% Stockhausen Favor 880 particulate superabsorbent and 34% powderized Birch pulp were added through the separate distribution unit 42 at a ratio of about 7% to 93%, respectively, thereby obtaining an overall superabsorbent material loading or weight percent, in the finished web of about 60%. The reader is referred to PCT published application WO 00/62922 (U.S. Ser. No. 09/546,634), for embodiments of pulp-coated superabsorbent materials known in the art.

Figure 3:
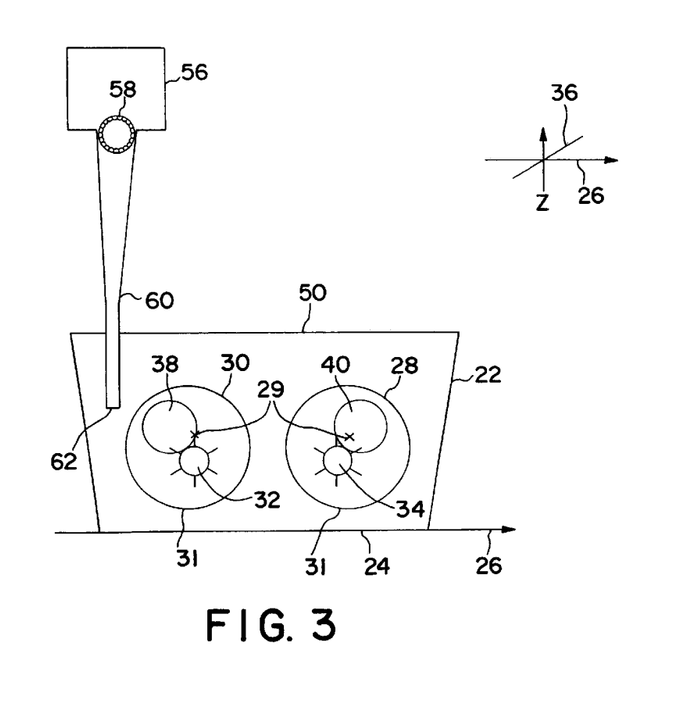
FIG. 3 is a schematic diagram of a third aspect of the present invention showing a Dan-Web type forming head with chute distribution means for absorbent particulates outside of, upstream of, and tangential to the tubular forming screens.

Referencing FIG. 3, a cross sectional view of a Dan-Web type head modified according to other aspects of the present invention, a forming head 22 is placed above a foraminous forming wire 24. As in the previous figures, the wire 24 collects the deposited web components discharged by the forming head 22 and moves in the machine direction 26 as indicated by arrows. The forming head overlays the wire 24 and extends across the width, or cross machine direction 36 of the wire. The forming head 22 contains two tubular forming screens 28, 30 having rotating distribution members 32, 34, one within each of the tubular forming screens 28, 30. The web component thermoplastic fibers and cellulosic fibers are entrained in an airstream and fed through openings 38, 40 into the tubular forming screens 28, 30 contained inside the forming head 22, to be distributed onto the wire 24.

The adding of particulates within the forming head 22 may be done via a separate distribution unit 56 including a metering distribution unit 58 and a placement chute 60 for placing the particulates into the forming head 22. The metering distribution unit 56 may include one or more of the components such as knurled roller, agitator, vibrator or wiper components as needed, and as set forth with respect to the hopper unit of FIGS. 1 and 5. The chute 60 may suitably have an outlet 62 outside of the tubular forming screens 28, 30 at a location upstream in the MD of the tubular forming screens, at or near the upstream edge 44 of the forming unit 22 and above the bottom-most surface 31 of the screens 28, 30, and more desirably above the center points 29 of the tubular forming screens 28, 30. The metering distribution unit 58 and the chute 60 may extend across the CD of the forming head 22 to deposit superabsorbents through the top 50 of the forming head. One suitable metering distribution unit may be a particle feeder from Christy Machine Co. of Fremont Ohio.

Figure 4:
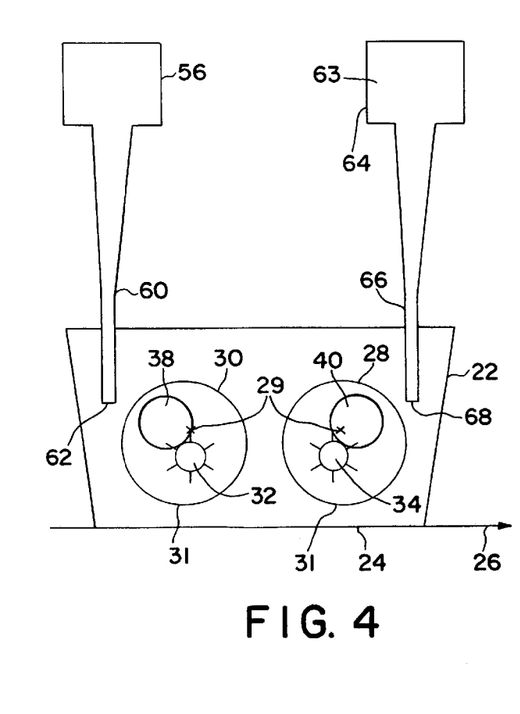
FIG. 4 is a schematic diagram of a fourth aspect of the present invention showing a Dan-Web type forming head with chute distribution means for absorbent particulates outside of, upstream and downstream of, and tangential to the forming screens.

Referencing FIG. 4, an aspect of the present invention is schematically illustrated wherein the particulates are added via both an upstream distribution unit 56 and a downstream distribution unit 64. The downstream distribution unit 64 will also suitably have a metering distribution unit 63 and a chute 66 having an outlet 68 placed above the bottom of the screens 28, 30, and more desirably above the center points 29 of the tubular forming screens 28, 30, and upstream and downstream of, collectively referred to as "beyond", the center points 29 of the upstream and downstream tubular forming screens 30, 28, respectively. Placement of the particulates within the forming head 22 via the chutes 60, 66 will help isolate the particulate addition stream and keep it from disrupting, or being disrupted by, the air flow existing within the forming head 22. The upstream distribution unit 56 and the downstream distribution unit 64 may operate to meter the flow of the superabsorbent particulates and may be operated concurrently, sequentially, or otherwise, such as to vary the amount, type, or placement of the particulates within the web.

Figure 6:
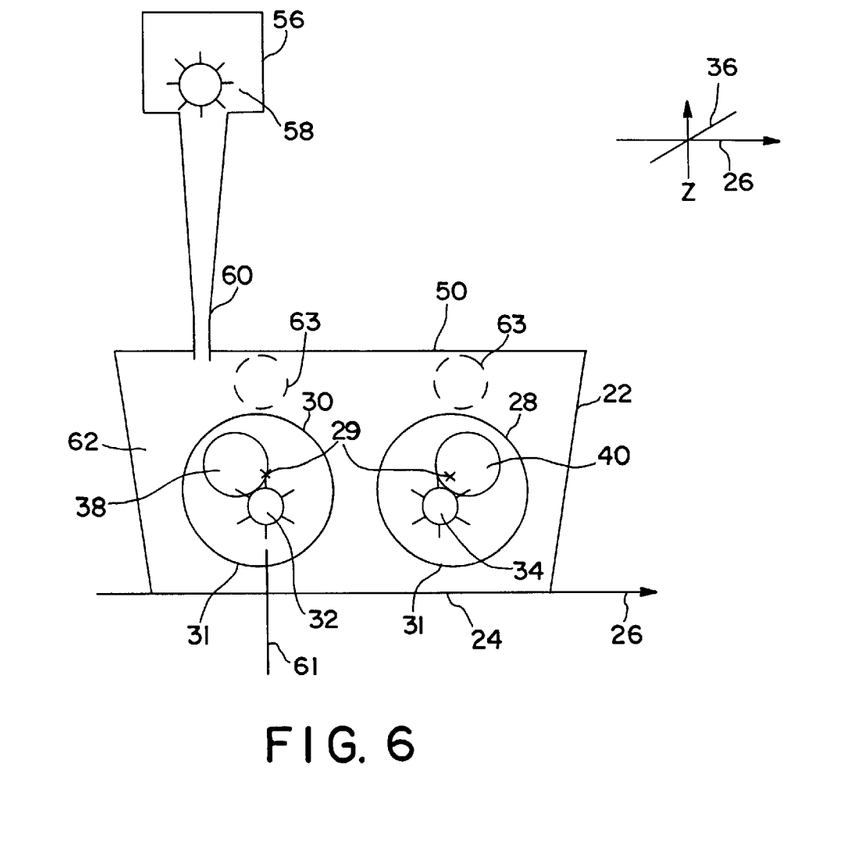
FIG. 6 is an alternative embodiment of FIG. 3 showing a presently preferred location of the chute distribution means.

Referencing FIG. 6, an alternative placement of the chute 60 is shown for adding particulate materials within the forming head 22 outside of the tubular forming screens 28, 30 at a location upstream in the machine direction beyond the center line 61 of the upstream tubular forming screen 30. The center line 61 is defined as a plane perpendicular to a forming wire 24 which collects and forms the web and perpendicular to the machine direction 26. The placement of the outlet of the chute 60 is above a bottom-most surface 31 of the tubular forming screens and more desirably above the center points 29 of the tubular forming screens 28, 30, and preferably, in this aspect of the invention, proximal to the top 50 of the forming head 22, and forty five degrees off the center line 61 on the upstream side. A second chute (not shown) may be similarly placed off the centerline on the downstream side of the downstream tubular forming screen 28. Placement of the chutes may in some instances be practically limited by other components of the forming head 22 such as cleaning brushes 63 (indicated in phantom) for the tubular forming screens 28, 30, but placement of the chutes at any point above the tubular forming screens 28, 30; such as between the nine and twelve o'clock positions of tubular forming screen 30 and the twelve and three o'clock positions of tubular forming screen 28; is contemplated to be within the scope of the present invention. Further the chutes are contemplated to be alternatively embodied as air entrainment units, rather than mechanically operated, so long as the air velocity of particulate entrainment is substantially neutral to the flow of air patterns existing elsewhere within the forming head 22 to distribute the other web constituents.

Preferred binder fibers for inclusion in the webs of the present invention are those having a relatively low melting point such as polyolefin fibers. Lower melting point polymers provide the ability to bond the fabric together at fiber cross-over points upon the application of heat. In addition, fibers having a lower melting polymer, like conjugate and biconstituent fibers are suitable for practice of this invention. Fibers having a lower melting polymer are generally referred to as "fusible fibers". By "lower melting polymers" what is meant are those having a melting temperature less than about 175 degrees C. It should be noted that the texture of the absorbent web can be modified from soft to stiff through selection of the glass transition temperature of the polymer. Exemplary binder fibers include conjugate fibers of polyolefins, polyamides and polyesters. Some suitable binder fibers are sheath core conjugate fibers available from KoSa Inc. under the designation T-255 and T-256 or copolyester designation, though many suitable binder fibers are known to those skilled in the art, and are available from many manufacturers such as Chisso Corporation, Osaka, Japan, and Fibervisions LLC of Wilmington, Del. A particularly suitable co-polyester binder fiber has been developed by KoSa as a sheath core application and is known by designation T-255.

Cellulosic wood pulps include standard softwood fluffing grade such as CR-1654 (US Alliance Pulp Mills, Coosa, Ala.). Pulp may be modified in order to enhance the inherent characteristics of the fibers and their processability. Curl may be imparted to the fibers by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylolated compounds such as urea or urea derivatives, dialdehydes such as maleic anhydride, non-methylolated urea derivatives, citric acid or other polycarboxylic acids. Some of these agents are less preferable than others due to environmental and health concerns. Pulp may also be stiffened by the use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are fully debonded pulp (NF405) and non-debonded pulp (NB416) and PH Sulfite pulp, also from Weyerhaeuser. HPZ3 from Buckeye Technologies, Inc. of Memphis, Tenn., has a chemical treatment that sets in a curl and twist, in addition to imparting added dry and wet stiffness and resilience to the fiber. Another suitable pulp is Buckeye HPF2 pulp and still another is IP SUPERSOFT® from International Paper Corporation.

The superabsorbent materials can be natural, synthetic and modified natural polymers and materials. In addition, the superabsorbent materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic superabsorbent material polymers include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthum gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,633 issued Feb. 28, 1978 to Masuda et al. and U.S. Pat. No. 4,286,082 issued Aug. 25, 1981 to Tsubakimoto et al.

Superabsorbent materials may be xerogels which form hydrogels when wetted. The term "hydrogel," however, has commonly been used to also refer to both the wetted and unwetted forms of the superabsorbent polymer material. Superabsorbent materials can be in many forms such as flakes, powders, particulates, fibers, continuous fibers, networks, solution spun filaments and webs. The particles can be of any desired shape, for example, spiral or semi-spiral, cubic, rod-like, polyhedral, etc. Needles, flakes, fibers, and combinations may also be used.

As will be appreciated by those skilled in the art, changes and variations to the invention are considered to be within the ability of those skilled in the art. Such changes and variations are intended by the inventors to be within the scope of the invention.

We claim:

1. A process for forming an absorbent web, the web having a first material and a particulate material, on a forming wire; comprising:

a) passing the first material entrained in an airstream through tubular forming screens contained inside a forming head, the tubular forming screens having rotating distribution members within the tubular forming screens; and b) adding the particulate material into the forming head outside of, and above the center point of, the tubular forming screens.

2. The process for forming an absorbent web according to claim 1 wherein the particulate material is metered.

3. The process for forming an absorbent web according to claim 2 wherein the particulate material is metered by a roller and a wiper.

4. The process for forming an absorbent web according to claim 1 wherein the particulate material is delivered upstream of a centerline of an upstream tubular forming screen in the machine direction.

5. The process for forming an absorbent web according to claim 4 wherein the particulate material is further delivered downstream of a centerline of a downstream tubular forming screen in the machine direction.

6. The process for forming an absorbent web according to claim 1 wherein the particulate material is delivered downstream of a centerline of a downstream tubular forming screen in the machine direction.

7. The process for forming an absorbent web according to claim 1 further including the first material comprising cellulosic fibers.

8. The process for forming an absorbent web according to claim 1 wherein the particulate material is a coated particulate superabsorbent material.

9. The process for forming an absorbent web according to claim 8 further including adding the particulate material by a hopper having an agitator.

10. The process for forming an absorbent web according to claim 8 further including adding the particulate material by a hopper having a vibrator.

11. The process for forming an absorbent web according to claim 1 wherein the particulate material is a particulate superabsorbent material.

12. The process for forming an absorbent web according to claim 1 wherein the particulate superabsorbent material is about 20% to about 98% superabsorbent material and about 2% to about 80% pulp.

13. The process for forming an absorbent web according to claim 1 wherein the first material comprises thermoplastic fibers.

14. The process for forming an absorbent web according to claim 13 wherein the thermoplastic fibers are bicomponent fibers.

15. The process for forming an absorbent web according to claim 1 wherein the particulate material is added into the forming head at a substantially neutral velocity.

16. The process for forming an absorbent web according to claim 1 wherein the absorbent web is between 75 gsm and 900 gsm basis weight.

17. The process for forming an absorbent web according to claim 1 wherein the absorbent web comprises greater than or equal to about 2 weight percent thermoplastic binder fiber, and less than or equal to about ninety eight weight percent absorbent material.

18. The process for forming an absorbent web according to claim 17 wherein the absorbent materials comprise between about 2 weight percent and about 70 weight percent cellulosic pulp and comprise between about 30 weight percent and about 98 weight percent superabsorbent material.

19. A process for forming an absorbent web, the web having a first material and a particulate material, on a forming wire; comprising:

a) passing the first material entrained in an airstream through tubular forming screens contained inside a forming head, the tubular forming screens having rotating distribution members within the tubular forming screens; and b) adding the particulate material into the forming head outside of the tubular forming screens at a location upstream or downstream in the machine direction beyond at least one center line of one of the tubular forming screens, the center line being a plane perpendicular to a forming wire for collecting the web and a machine direction, the particulate material being added via a chute placed above a center point of the tubular forming screens.

20. The process for forming an absorbent web according to claim 19 further comprising:

adding the particulate material into the forming head via a chute opening proximal to the top of the forming head.

21. The process for forming an absorbent web according to claim 20 further comprising:

adding the particulate material into the forming head outside of the tubular forming screens at locations upstream and downstream in the machine direction of the tubular forming screen center lines.

22. The process for forming an absorbent web according to claim 19 further comprising:

adding the particulate material into the forming head outside of the tubular forming screens at locations upstream and downstream in the machine direction of the tubular forming screen center lines.

23. The process for forming an absorbent web according to claim 19 wherein the particulate material is added into the forming head at a substantially neutral velocity.

24. An apparatus for forming an absorbent web, the web having a first material and a particulate material, on a forming wire; comprising:

a) a forming head containing tubular forming screens therein, the tubular forming screens having means for accepting an airstream of entrained first material, the tubular forming screens having rotating distribution members therein; and b) a distribution unit for adding the particulate material into the forming head outside of the tubular forming screens at locations above center points of the tubular forming screens.

25. The apparatus for forming an absorbent web according to claim 24 further comprising:

the distribution unit further being located at a location upstream in the machine direction from the center point of an upstream tubular forming screen.

26. The apparatus for forming an absorbent web according to claim 24 further comprising:

the distribution unit further being located at a location downstream in the machine direction from the center point of a downstream tubular forming screen.

27. The apparatus for forming an absorbent web according to claim 25 further comprising:

a second distribution unit for adding particulate material into the forming head outside of the tubular forming screens at locations above the center points of the tubular forming screens;

the second distribution unit further being located at a location downstream of the center point in the machine direction from a downstream tubular forming screen.

28. The apparatus for forming an absorbent web according to claim 24 further including a metering system for the particulate material.

29. The apparatus for forming an absorbent web according to claim 24 wherein the distribution unit for adding particulate material further comprises a chute.

30. The apparatus for forming an absorbent web according to claim 29 wherein the distribution unit further comprises an agitator.

31. The apparatus for forming an absorbent web according to claim 29 wherein the distribution unit further comprises a vibrator.

32. The apparatus for forming an absorbent web according to claim 29 wherein the distribution unit further comprises a metering roller and a wiper.

* * * * *